US010779736B2

(12) United States Patent
Koskelainen et al.

(10) Patent No.: US 10,779,736 B2
(45) Date of Patent: Sep. 22, 2020

(54) DEVICE AND METHOD FOR NON-INVASIVE MONITORING OF RETINAL TISSUE TEMPERATURE

(71) Applicant: AALTO UNIVERSITY FOUNDATION SR, Aalto (FI)

(72) Inventors: Ari Koskelainen, Huhmari (FI); Marja Pitkänen, Aalto (FI)

(73) Assignee: AALTO UNIVERSITY FOUNDATION SR, Aalto (FI)

( * ) Notice: Subject to any disclaimer, the term of this patent is extended or adjusted under 35 U.S.C. 154(b) by 294 days.

(21) Appl. No.: 15/570,702

(22) PCT Filed: Apr. 29, 2016

(86) PCT No.: PCT/FI2016/050275
§ 371 (c)(1),
(2) Date: Oct. 30, 2017

(87) PCT Pub. No.: WO2016/174310
PCT Pub. Date: Nov. 3, 2016

(65) Prior Publication Data
US 2018/0289265 A1    Oct. 11, 2018

Related U.S. Application Data

(60) Provisional application No. 62/154,740, filed on Apr. 30, 2015.

(51) Int. Cl.
*A61B 5/01*    (2006.01)
*A61B 3/10*    (2006.01)
(Continued)

(52) U.S. Cl.
CPC ............... *A61B 5/01* (2013.01); *A61B 3/10* (2013.01); *A61B 5/0496* (2013.01);
(Continued)

(58) Field of Classification Search
CPC ........ A61F 9/00821; A61F 2009/00844; A61F 2009/00863; A61B 3/10;
(Continued)

(56) References Cited

U.S. PATENT DOCUMENTS

| 6,733,490 B1 | 5/2004 | Falsini et al. | |
| 7,465,299 B2 * | 12/2008 | Rovati | A61F 9/008 351/211 |
| 2003/0078567 A1 * | 4/2003 | Dorin | A61F 9/008 606/4 |

FOREIGN PATENT DOCUMENTS

| WO | 0126591 A1 | 4/2001 | |
| WO | WO-0126591 A1 * | 4/2001 | ............. A61F 9/008 |

* cited by examiner

*Primary Examiner* — Christine H Matthews
*Assistant Examiner* — Joshua Daryl D Lannu
(74) *Attorney, Agent, or Firm* — Berggren LLP

(57) ABSTRACT

A method and device for non-invasive monitoring of the temperature of the retina and the retinal pigment epithelium inside the eye, particularly during heating of the bottom of the eye, wherein alternating probing short-duration pulses of light, one at wavelength close to the absorption maximum of the photoreceptor cell type and the other at wavelength in the near-infrared region, are directed at the retinal tissue at appropriate time intervals. Photoreceptor cell electrical signals, photoresponses, are recorded using electroretinography (ERG) and the changes in retinal temperature are determined from changes in photoresponse kinetics and changes in photoreceptor sensitivity to the stimuli. The method is especially applicable at temperatures up to 45° C. for humans and for other animals.

20 Claims, 2 Drawing Sheets

(51) Int. Cl.
*A61N 5/06* (2006.01)
*G01K 13/00* (2006.01)
*A61F 9/008* (2006.01)
*A61B 5/0496* (2006.01)
*A61B 18/00* (2006.01)
*A61N 5/067* (2006.01)

(52) U.S. Cl.
CPC ........ *A61F 9/00821* (2013.01); *A61N 5/0625* (2013.01); *G01K 13/002* (2013.01); *A61B 2018/00642* (2013.01); *A61B 2018/00791* (2013.01); *A61F 2009/00844* (2013.01); *A61F 2009/00863* (2013.01); *A61N 2005/067* (2013.01); *A61N 2005/0651* (2013.01); *A61N 2005/0659* (2013.01); *A61N 2005/0662* (2013.01)

(58) Field of Classification Search
CPC ........... A61B 2018/00791; A61B 2018/00642; A61B 5/0496; A61B 5/01; A61N 2005/067; A61N 2005/0662; A61N 5/0625; A61N 2005/0651; A61N 2005/0659; G01K 13/002
See application file for complete search history.

DEVICE AND METHOD FOR NON-INVASIVE MONITORING OF RETINAL TISSUE TEMPERATURE

PRIORITY

This application is a U.S national application of the international application number PCT/FI2016/050275 filed on Apr. 29, 2016 and claiming priority of U.S. provisional application 62/154,740 filed on Apr. 30, 2015, the contents of both of which are incorporated herein by reference.

TECHNICAL FIELD OF THE INVENTION

The invention relates to a device and method for non-invasive monitoring of retinal tissue and retinal pigment epithelium temperature. Additionally the invention relates to an arrangement for controlling a heating device for heating the retinal tissue area and especially the retinal pigment epithelium area of interest inside an eye.

The invention will find applications for example in the field of medical interventions, where e.g. by means of electromagnetic radiation, e.g. by laser light or by light from light emitting diodes (LEDs), temperature elevations can be produced and simultaneously monitored and controlled in the retina and in the retinal pigment epithelium of the eye.

BACKGROUND OF THE INVENTION

There has been a long-felt need e.g. in laser eye therapy among other to monitor the retinal tissue and retinal pigment epithelium temperature during the procedure, such as in a therapy in connection with degeneration of retinal pigment epithelium which is treated by heating. Especially with the heating therapy it is particularly important to monitor the temperature of the retinal pigment epithelium very accurately and in a reliable manner so that no harmful effects will be caused due to overheating.

Only very few methods for monitoring the retinal pigment epithelium temperature are known from prior art. U.S. Pat. No. 7,465,299 B2 discloses a method for measuring retinal temperature, where secondary emitted light emanating from retinal tissue is first generated, after which the secondary emitted light emanating from the retinal tissue is detected. The temperature determination is then based on statistical analysis of temporal fluctuation of the scattered and detected secondary emitted light. Specifically, the temperature of the retinal tissue is determined by statistically analysing the secondary emitted light.

There are however some disadvantages and challenges relating to the prior art. At first the retinal tissue area and especially the retinal pigment epithelium locates inside and in the back of an eye, which is very difficult area to read. In addition there is a very effective thermal or heat transfer just behind only few µm (micrometer) layer of the retinal tissue due to effective blood circulation, which causes easily inaccuracies to readings of actual temperatures in the thin layer of the retinal tissue and especially in the retinal pigment epithelium, because there is a very big risk to read the temperature value from a wrong layer with different temperature.

SUMMARY OF THE INVENTION

An object of the invention is to alleviate and eliminate the problems relating to the known prior art. Especially the object of the invention is to provide a method and device for determination of the retinal tissue temperature inside an eye in a non-invasive, fast, accurate and reliable way so that the temperature is in fact determined from the cells of the retinal tissue or retinal pigment epithelium and not from the wrong depth behind the layers of the retinal tissue or retinal pigment epithelium.

The object of the invention can be achieved by the features of independent claims.

The invention relates to a method for non-invasive determination of retinal tissue temperature inside an eye according to claim 1. In addition the invention relates to a device and computer program product for non-invasive determination of retinal tissue temperature inside an eye according to claims 8 and 18, as well as to an arrangement for controlling heating power of an heating apparatus used for heating the retinal tissue inside an eye according to claim 17.

According to an embodiment of the invention the retinal tissue (including retinal pigment epithelium) temperature inside an eye is determined non-invasively. The determination or monitoring is advantageously done e.g. during heating of the bottom of the eye, wherein stimulus or stimuli of electromagnetic radiation is/are directed at the retinal tissue at appropriate time intervals (later stimulus, stimuli or stimulation). The stimulation may comprise e.g. alternating short-duration pulses or continuous fluctuating illumination, consisting e.g. sequences of pulses, or having continuously changing intensity. As an example the stimulation may be continuous and having one or more wavelengths, such as having white light or certain visible wavelength, or infrared wavelength. In addition the stimulation may be a continuous illumination with a first wavelength or a first wavelength range, and changing to a second wavelength or to as second wavelength range. Moreover it should be noted that the stimulation may be a continuous light stimulus with fluctuating stimulus strength (intensity), e.g. sequences of pseudorandom, sinusoidal, sawtooth, or stepwise light stimuli, for example.

Photoreceptor cell electrical signals, photoresponses, are then recorded using e.g. an electroretinography (ERG) device and the changes in retinal temperature are determined from changes in photoresponse kinetics and/or changes in photoreceptor sensitivity to the stimulus. The method is especially applicable at temperatures up to 45° C. for humans and for other animals.

The measurements and determinations are based on that fact that the rates of biochemical reactions are temperature-dependent. The neural signalling mechanisms generating electrical responses to absorption of photons (light) in the photoreceptor cells, rods and cones, consist of cascades of biochemical reactions, making the kinetics of the electrical photoresponses of the photoreceptor cells temperature-dependent: The photoresponse kinetics gets faster towards higher temperatures.

Another temperature-dependent feature in photoreceptor signalling, fully independent of the previous one, is photoreceptor sensitivity at long wavelengths, i.e. the stimulus. The generation of the visual signal is started by absorption of photons to visual pigment molecules. Above certain wavelengths, i.e. below certain photon energy, the energy of a photon alone is not enough to excite the visual pigment molecule in the photoreceptor cell and the extra energy in addition to photon energy needed for excitation of the visual pigment molecule comes from thermal energy, making the probability of photon absorption higher and thus increasing photoreceptor sensitivity towards higher temperatures at long wavelengths, typically above 600-650 nm.

The photoreceptor layer of the retina is in tight contact with the pigment epithelium in the vertebrate eye and the photoreceptor cell outer segments containing the visual pigment and the phototransduction machinery generating the electrical signal in photoreceptor cells are partly embedded in the pigment epithelium. Since there is no blood circulation in the pigment epithelium and in the photoreceptor layer, the temperatures of photoreceptor cells and the pigment epithelium cells are the same or very close to each other.

According to an embodiment the region of the retina of interest is stimulated by an electromagnetic radiation (light) stimulus, for example short-duration pulses in the range from a one or few μs to a few ms or continuous fluctuating light, and the responses to light stimulation are recorded using e.g. electroretinography, e.g. corneal ERG. The recorded ERG signal is conducted to a determination unit, such as a computer, and the temperature-dependent features of the ERG photoresponses are analyzed to determine the temperature of the retinal tissue. The method can be used, for example, to monitor temperature changes in the retinal pigment epithelium and the retina during heat treatment by near-infrared radiation directed to the eye from e.g. lasers or light emitting diodes.

In the case the pigment epithelium is heated by transpupillary irradiation, the wavelength of the heating irradiation should consist of such a long wavelength light that the heating radiation itself does not excessively stimulate photoreceptors.

According to an embodiment electromagnetic radiation stimulus is provided to interact with the retinal tissue (or also retinal pigment epithelium; later only retinal tissue is used for both). Electrical photoresponses of the retinal tissue to the electromagnetic radiation stimulus are then recorded using e.g. electroretinography as a function of time. The electrical photoresponses are advantageously temperature-dependent photoresponses of the retinal tissue to the changes in electromagnetic radiation stimulation (either pulses or continuous fluctuating light). After this a first and/or second parameter of the measured photoresponses are determined.

The first parameter relates to kinetics (such as speed or rate or response time) of the measured electrical photoresponses of the retinal tissue to the electromagnetic radiation stimulation, and the second parameter relates to photoreceptor sensitivity (in practice to the amplitude) of the measured electrical photoresponses of the retinal tissue to the electromagnetic radiation stimulation, more advantageously to the ratio of photoreceptor sensitivity to near-IR light stimuli (consisting of photons with energies too low to excite the visual pigment molecules without extra thermal energy) and of photoreceptor sensitivity to light stimuli with photon energies high enough to excite the visual pigment molecules alone.

According to an advantageous embodiment the temperature of the retinal tissue is determined then based on the determined first and/or second parameter of the measured photoresponse by comparing the determined first and/or second parameter (kinetic/rate and/or sensitivity/amplitude) to previously determined first and/or second reference parameter, where the dependency of said previously determined first and/or second reference parameter on the temperature is known.

As an example the used wavelength of the first electromagnetic radiation stimulus is close to the absorption maximum of the photoreceptor cell type and advantageously in the range of 500-600 nm. Depending on the application, the range may be of 520-550 nm, or around 530 nm. In addition, as an example, the wavelength of the second electromagnetic radiation stimulus is in the near-infrared region and advantageously above 650 nm or 700 nm.

It is to be noted that the first parameter relating to the kinetics reflects essentially changes in photoresponse kinetics and is e.g. time-to-peak or the time to the maximal slope of the measured wave from the electromagnetic radiation pulse stimulus.

The present invention offers advantages over the known prior art, such as the possibility to measure the local temperature of the retinal tissue and especially the retinal pigment epithelium that locates inside and in the back of an eye, easily, non-invasively and especially accurately and in a reliable manner. In addition the method and device of the invention can be used for controlling heating power of a heating apparatus used for heating retinal tissue inside an eye so that the temperature is kept in a predetermined range, such as advantageously above 37° C. and below 45° C.

The exemplary embodiments presented in this text are not to be interpreted to pose limitations to the applicability of the appended claims. The verb "to comprise" is used in this text as an open limitation that does not exclude the existence of also unrecited features. The features recited in depending claims are mutually freely combinable unless otherwise explicitly stated.

The novel features which are considered as characteristic of the invention are set forth in particular in the appended claims. The invention itself, however, both as to its construction and its method of operation, together with additional objects and advantages thereof, will be best understood from the following description of specific example embodiments when read in connection with the accompanying drawings.

BRIEF DESCRIPTION OF THE DRAWINGS

Next the invention will be described in greater detail with reference to exemplary embodiments in accordance with the accompanying drawings, in which.

DETAILED DESCRIPTION

Figure 1:
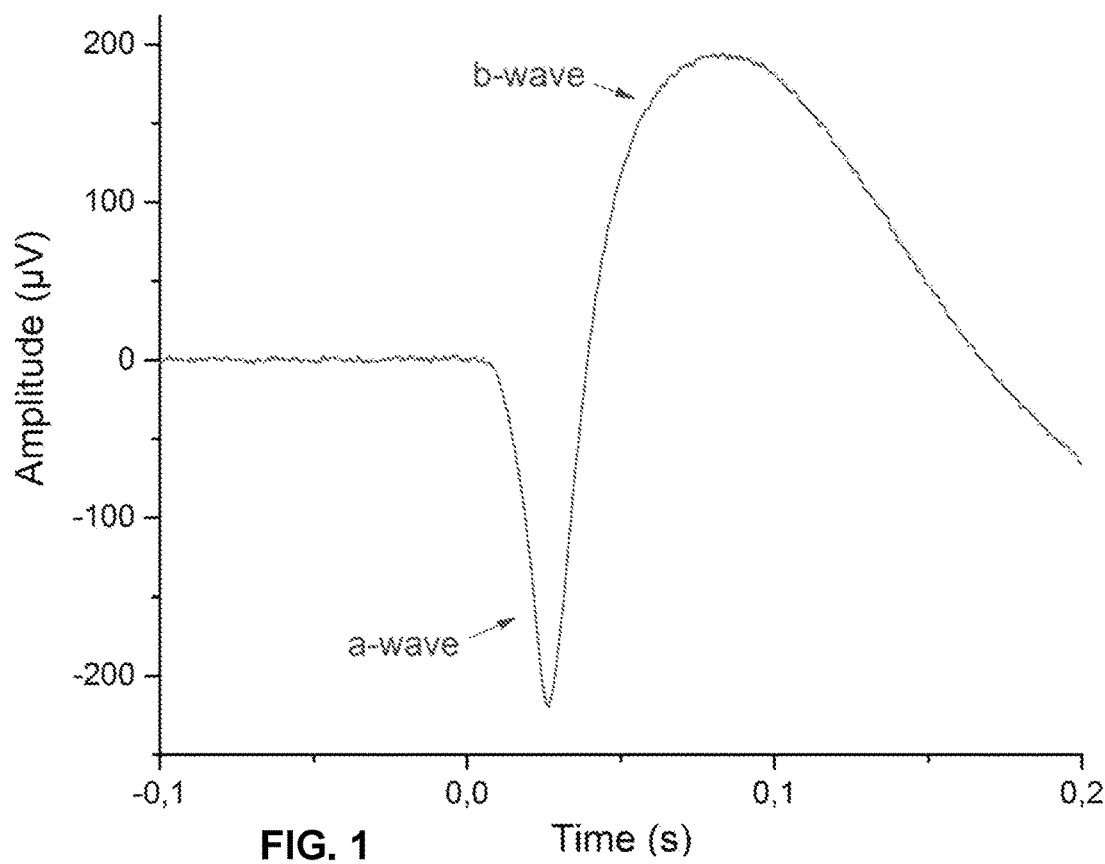
FIG. 1 illustrates a principle of an exemplary ERG signal recorded from a mouse retina showing the a-wave and the b-wave according to an advantageous embodiment of the invention.

FIG. 1 illustrates a principle of an exemplary ERG signal recorded from a mouse retina showing the a-wave and the b-wave according to an advantageous embodiment of the invention. According to an embodiment, the temperature of the photoreceptor layer and/or the retinal pigment epithelium can be determined combining temperature information deduced from changes in photoresponse kinetics and changes in photoreceptor sensitivity. When gaining temperature estimates from long-wavelength sensitivity best resolution is achieved when short-duration pulses of light weak enough to produce linear range b-wave responses are used, i.e. the amplitude of the responses should not be larger than approximately 15% of the maximal amplitude attainable with strong stimuli.

For gaining temperature estimates from photoresponse kinetics, changes in a-wave or b-wave kinetics or in both can be analyzed. Best resolution is achieved with linear-range b-wave responses, because in the linear range the photoresponse kinetics does not depend on stimulus strength but depends only on temperature. Several features or combinations of features reflecting changes in photoresponse kinetics can be used, e.g. the time-to-peak of the a-wave or b-wave from the light pulse, the time to the maximal slope of the a-wave or the b-wave etc.

In order to continuously monitor the temperature, the electromagnetic radiation stimulation is given as pulses or changed (e.g. intensity or wavelength is changed) essentially at constant time intervals, where the time intervals are in the range of 1-15 s, more advantageously in the range of 1-5 s. Another possibility is to use continuous light stimuli with fluctuating stimulus strength (e.g. sequences of pseudorandom, sinusoidal, sawtooth, or stepwise light stimuli).

Figure 2:
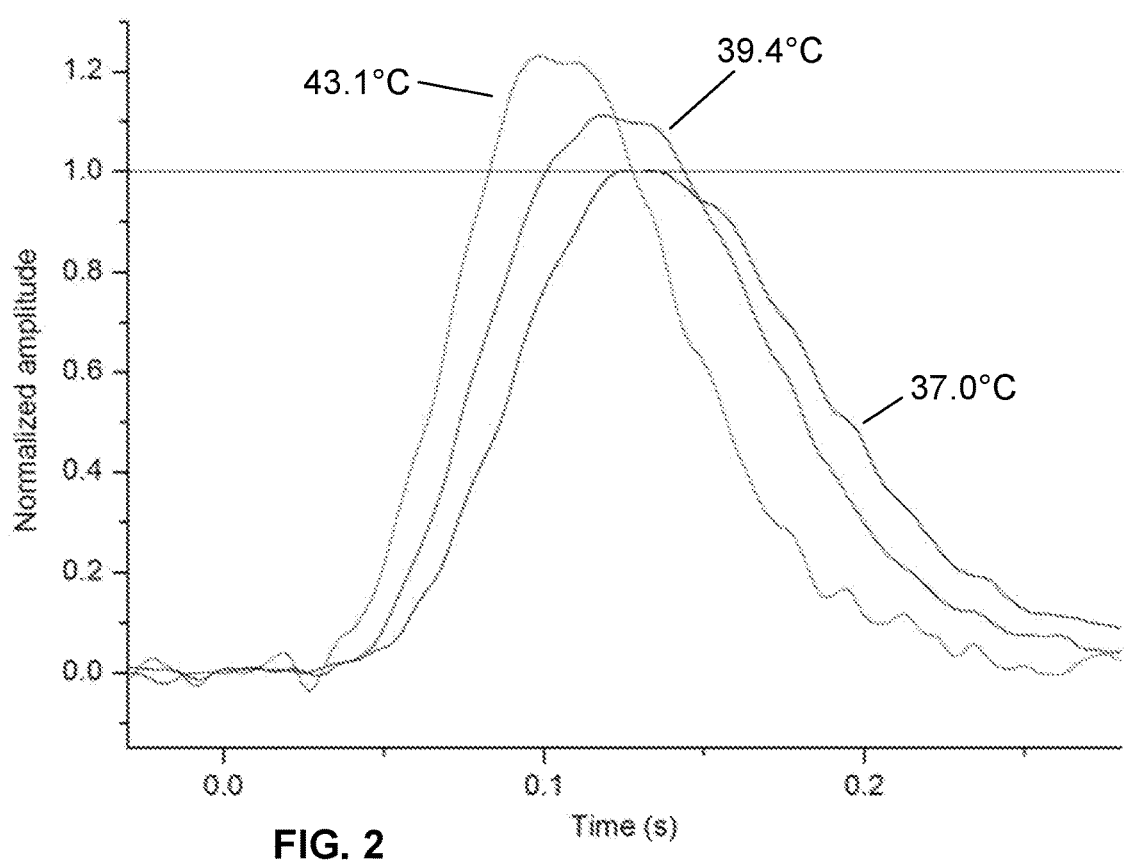
FIG. 2 illustrates exemplary ERG signals recorded from a mouse retina showing the effects of temperature on b-wave kinetics and on rod photoreceptor sensitivity at long wavelengths (780 nm) according to an advantageous embodiment of the invention.

FIG. 2 illustrates exemplary ERG signals recorded from a mouse retina showing the effects of temperature on b-wave kinetics and on rod photoreceptor sensitivity at long wavelengths (780 nm) according to an advantageous embodiment of the invention, where the changes in kinetics (rate or response time) as well as also in photoreceptor sensitivity (the amplitude) can be clearly seen, when the retina is heated.

Figure 3:
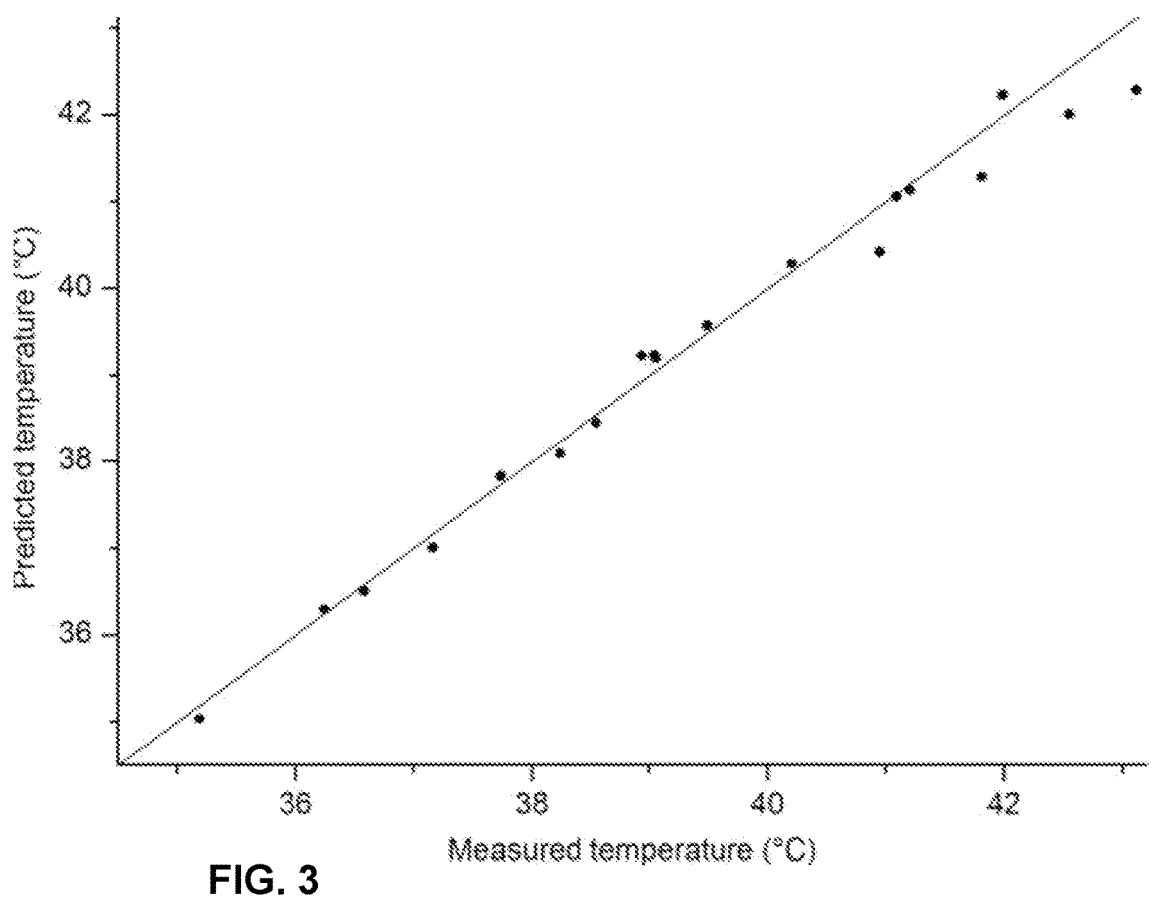
FIG. 3 illustrates an exemplary graph showing comparison of measured temperature data with temperature data determined by combining photoresponse kinetics and long-wavelength sensitivity data from one isolated mouse retina according to an advantageous embodiment of the invention.

FIG. 3 illustrates an exemplary graph showing comparison of measured temperature data with temperature data determined by combining photoresponse kinetics and long-wavelength sensitivity data from one isolated mouse retina according to an advantageous embodiment of the invention.

Figure 4:
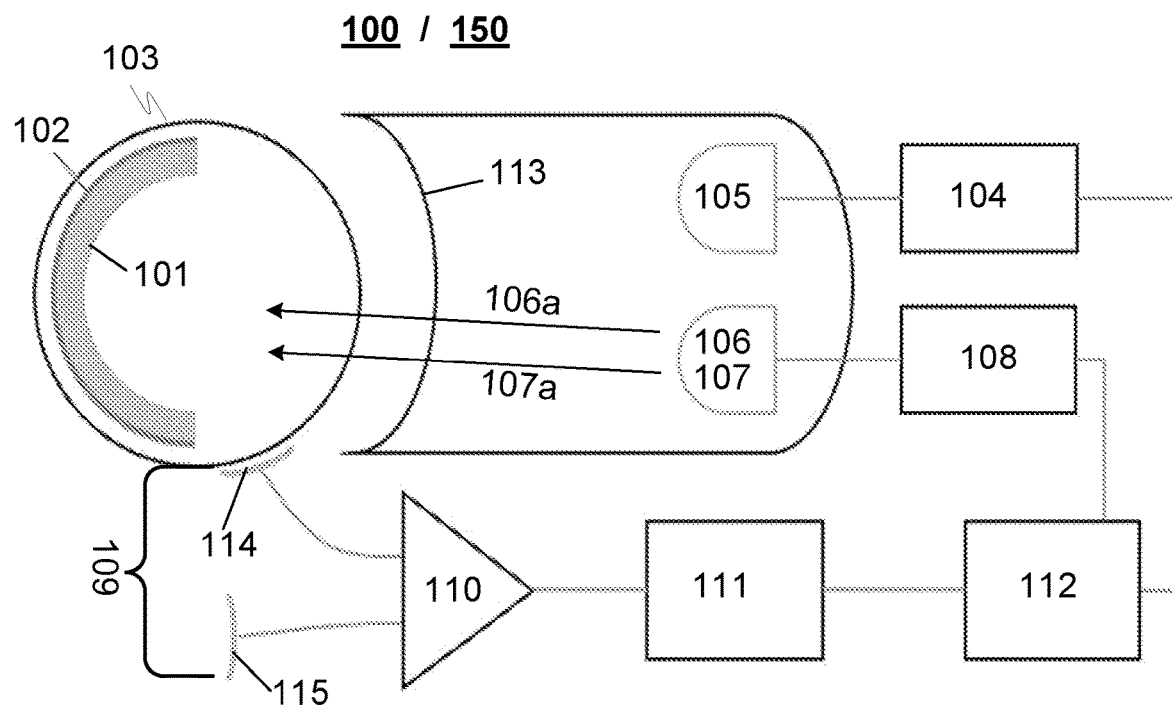
FIG. 4 illustrates an exemplary device for non-invasive determination of retinal tissue temperature inside an eye as well as an arrangement using the device for controlling heating power of a heating apparatus used for heating retinal tissue inside an eye according to an advantageous embodiment of the invention.

FIG. 4 illustrates an exemplary device 100 for non-invasive determination of the retinal tissue 101, 102 temperature inside an eye 103 as well as an arrangement 150 using the device 104 for controlling the heating power of a heating apparatus (e.g. an IR LED) 105 used for heating a retinal tissue inside an eye according to an advantageous embodiment of the invention. The device 100 for non-invasive determination of a retinal tissue (including also the retinal pigment epithelium) temperature inside an eye comprises a first and/or second electromagnetic radiation sources 106, 107 (with suitable controller 108) for providing the electromagnetic radiation stimulation, such as first and/or second electromagnetic radiation stimuli 106a, 107a to interact with the retinal tissue 101, 102. It is to be noted that the all kinds of stimulation can be provided, as is depicted elsewhere in this document. In addition the device comprises a measuring member 109, such as an electroretinography device, for measuring electrical photoresponses of the retinal tissue 101, 102 to the electromagnetic radiation stimulation as a function of time.

The measuring member 109 may be implemented by an electroretinography device, such as a corneal electroretinography device. The device may comprise an ERG electrode 114 located on the surface of the eye under study and a reference electrode 115 located somewhere else in contact with the body. According to an embodiment the changes in potentials (voltage) between these electrodes (114, 115) are then measured as a response to the stimulation.

The device also comprises a first determination unit 111, such as a computer with suitable software, for determining a first and/or second parameter of the measured photoresponse. In addition the device comprises also a second determination unit 112, such as a computer with suitable software (can be the same as the first determination unit), for determining the temperature of the retinal tissue based on the determined first and/or second parameter of the measured photoresponse. The determination can be implemented as depicted elsewhere in this description. In addition the device advantageously comprises suitable electronics, such as an amplifier and A/D converters 110.

The device advantageously comprises also a controller 108 for controlling the second electromagnetic stimulation, such as its intensity, fluctuation, duration as well other parameters. For example the stimulation can be controlled so to provide e.g. the first and second electromagnetic radiation pulses/stimuli so that they are provided as alternating pulses/stimuli at appropriate time intervals, where said appropriate time intervals are controlled to be e.g. in the range of 1-15 s, for example. The first and second electromagnetic radiation sources 106, 107 are advantageously implemented by LED-diodes and/or laser sources, but also other and suitable electromagnetic radiation sources can be used.

The device may also comprise optical members 113, such as lenses and/or prisms, for directing the provided electromagnetic radiation stimuli 106a, 107a to the retinal tissue 101, 102.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims. In particularly it should be noted that the provided electromagnetic radiation stimulation may comprise e.g. alternating short-duration pulses or continuous fluctuating illumination, consisting e.g. sequences of pulses, or having continuously changing intensity, having one or more wavelengths, or wavelength area or areas, as described in the document.

The features recited in dependent claims are mutually freely combinable unless otherwise explicitly stated.

The invention claimed is:

1. A method for non-invasive determination of a retinal tissue temperature inside an eye, comprising:
    providing an electromagnetic radiation stimulation to interact with a retinal tissue,
    measuring an electrical response of the retinal tissue to the electromagnetic radiation stimulation as a function of time, wherein the electrical response is a temperature-dependent electrical response of the retinal tissue to a used electromagnetic radiation stimulation,
    determining a first and a second parameter of a measured response, wherein
    the first parameter is a kinetics of the measured electrical response of the retinal tissue to the electromagnetic radiation stimulation, and
    the second parameter is a photoreceptor sensitivity parameter of the measured electrical response of the retinal tissue to the electromagnetic radiation stimulation,
    determining the temperature of the retinal tissue based on the determined first and the second parameter of the measured electrical response by:

comparing at least the determined first parameter to a previously determined first reference parameter, wherein a temperature dependency of said previously determined first reference parameter is known, and comparing a ratio of said determined second parameter, said ratio being an electrical response to a first wavelength of the stimulation to a second parameter being an electrical response to a second wavelength of the stimulation, wherein a temperature dependency of said ratio of said second parameter is known.

2. The method of claim 1, wherein the electromagnetic radiation stimulation comprises:

the first wavelength and the second wavelength, comprising white light or a visible wavelength, or an infrared wavelength, the first wavelength or a first wavelength range changing to the second wavelength or to a second wavelength range, alternating short-duration pulses, continuous radiation with fluctuating or continuously changing intensity or wavelength, continuous radiation comprising sequences of pseudorandom, sinusoidal, sawtooth, or stepwise electromagnetic radiation stimuli, or sequences of pulses.

3. The method of claim 1, wherein a wavelength of a first electromagnetic radiation stimulation is in a range of an absorption maximum of a photoreceptor cell type.

4. The method of claim 3, wherein the wavelength of the first electromagnetic radiation stimulation is in a range of 500-600 nm.

5. The method of claim 1, wherein a wavelength of a second electromagnetic radiation stimulation is in a near-infrared region.

6. The method of claim 5, wherein the wavelength of the second electromagnetic radiation stimulation is above 600 nm.

7. The method of claim 1, wherein the electromagnetic radiation stimulation comprises first and second electromagnetic radiation alternating pulses, directed at the retinal tissue at time intervals in a range of 0.5-5 ms.

8. The method of claim 1, wherein the first parameter is a kinetics parameter of a time-to-peak or a time to a maximal slope of a measured wave from an electromagnetic radiation pulse stimulus.

9. The method of claim 1, wherein the determination of the retinal tissue temperature is a continuously monitored determination and the electromagnetic radiation stimulation is given or changed at constant time intervals.

10. The method of claim 9, wherein the time intervals are in a range of 0.5-15 s.

11. A device for non-invasive determination of a retinal tissue temperature inside an eye, comprising:

an electromagnetic radiation source for providing electromagnetic radiation stimulation to interact with a retinal tissue, a measuring member, being an electroretinography device, for measuring an electrical response of the retinal tissue to the electromagnetic radiation stimulation as a function of time, wherein the electrical response is a temperature-dependent response of the retinal tissue to a used electromagnetic radiation stimulation, and a first determination unit, being a computer with a software, for determining a first and a second parameter of a measured response, wherein the first parameter is a kinetics parameter of a measured electrical response of the retinal tissue to the electromagnetic radiation stimulation, and the second parameter is a photoreceptor sensitivity parameter of the measured electrical response of the retinal tissue to the electromagnetic radiation stimulation, a second determination unit, being a computer with a software, for determining the temperature of the retinal tissue based on the determined first and the second parameter of the measured electrical response by:

comparing at least the determined first parameter to a previously determined first reference parameter, wherein a temperature dependency of said previously determined first reference parameter is known, and comparing a ratio of said determined second parameter, said ratio being an electrical response to a first wavelength of the stimulation to a second parameter being an electrical response to a second wavelength of the stimulation, wherein a temperature dependency of said ratio of said second parameter is known.

12. The device of claim 11, wherein the device with the electromagnetic radiation source is configured to provide:

the first wavelength and the second wavelength, comprising white light or a visible wavelength, or infrared wavelength, the first wavelength or a first wavelength area changing to the second wavelength or to a second wavelength area, alternating short-duration pulses, continuous radiation with fluctuating or continuously changing intensity or wavelength, continuous radiation comprising sequences of pseudorandom, sinusoidal, sawtooth, or stepwise electromagnetic radiation stimuli, or sequences of pulses.

13. The device of claim 11, wherein the first and the second wavelength provided by the electromagnetic radiation source is in a range of 500-600 nm.

14. The device of claim 13, further comprising a reference electrode for measuring an electrical response of a reference retinal tissue to the electromagnetic radiation stimulation as a function of time, wherein he electrical response is a temperature-dependent response of the retinal tissue to the used electromagnetic radiation stimulation and wherein the temperature of said reference retinal tissue is known, whereupon the second determination unit is configured to determine the temperature of the retinal tissue by comparing the determined first and the second parameter to a determined first and a second reference parameter related to the reference retinal tissue.

15. The device of claim 11, wherein the wavelength provided by the electromagnetic radiation source is above 600 nm.

16. The device of claim 11, further comprising a controller for controlling said electromagnetic radiation stimulation, so that the stimulation is provided as alternating pulses at time intervals, wherein said time intervals are controlled to be in a range of 0.5-15 s.

17. The device of claim 11, wherein said electromagnetic radiation source comprises a LED-diode or a laser source.

18. The device of claim 11, further comprising optical members for directing electromagnetic radiation pulses to the retinal tissue.

19. The device of claim 11, wherein the measuring member comprises an electroretinography (ERG) device.

20. An arrangement for controlling heating power of a heating apparatus used for heating a retinal tissue inside an eye, wherein the arrangement comprises a device for non-invasive determination of the retinal tissue temperature inside the eye, said device comprising:
- an electromagnetic radiation source for providing electromagnetic radiation stimulation to interact with the retinal tissue,
- a measuring member, being an electroretinography device, for measuring an electrical response of the retinal tissue to the electromagnetic radiation stimulation as a function of time, wherein the electrical response is a temperature-dependent response of the retinal tissue to a used electromagnetic radiation stimulation, and
- a first determination unit, being a computer with a software, for determining a first and a second parameter of a measured electrical response, wherein
- the first parameter is a kinetics parameter of the measured electrical response of the retinal tissue to the electromagnetic radiation stimulation, and
- the second parameter is a photoreceptor sensitivity parameter of the measured electrical response of the retinal tissue to the electromagnetic radiation stimulation,
- a second determination unit, being a computer with a software, for determining the temperature of the retinal tissue based on the determined first and the second parameter of the measured electrical response by:
- comparing at least the determined first parameter to a previously determined first reference parameter, wherein a temperature dependency of said previously determined first reference parameter is known, and
- comparing a ratio of said determined second parameter, said ratio being an electrical response to a first wavelength of the stimulation to a second parameter being an electrical response to a second wavelength of the stimulation, wherein a temperature dependency of said ratio of said second parameter is known, and
- a power controller for controlling a heating power of said heating apparatus based on the determined retinal tissue temperature, so that the temperature is kept in a predetermined range.

* * * * *